United States Patent
Larsen

(10) Patent No.: US 9,938,238 B2
(45) Date of Patent: Apr. 10, 2018

(54) ANTI-AUXIN COMPOUNDS

(71) Applicant: THE REGENTS OF THE UNIVERSITY OF CALIFORNIA, Oakland, CA (US)

(72) Inventor: Paul Brian Larsen, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/264,395

(22) Filed: Sep. 13, 2016

(65) Prior Publication Data

US 2017/0073308 A1    Mar. 16, 2017

Related U.S. Application Data

(60) Provisional application No. 62/218,439, filed on Sep. 14, 2015.

(51) Int. Cl.
  *A01N 43/36* (2006.01)
  *A61K 31/40* (2006.01)
  *C07D 207/34* (2006.01)

(52) U.S. Cl.
  CPC .......... *C07D 207/34* (2013.01); *A01N 43/36* (2013.01)

(58) Field of Classification Search
  USPC ....................................... 514/423
  See application file for complete search history.

(56) References Cited

PUBLICATIONS

J. G. Cannon, Chapter Nineteen in Burgers Medicinal Chemistry and Drug Discovery, Fifth Edition, vol. I: Principles and Practice, Wiley-Interscience 1995, pp. 783-802.*
Calin, "Clinical Use of Tolmetin Sodium in Patients with Ankylosing Spondylitis: A Review," J Clin Pharmacol. 1983; 23:301-308.
Cardoe et al., "A Double-Blind Crossover Comparison of Tolmetin Sodium and Phenylbutazone in the Treatment of Rheumatoid Arthritis," Current Medical Research and Opinion, vol. 4, No. 10, 1977, 688-694.
Cordrey, "Tolmetin Sodium, a New Anti-Arthritis Drug: Double-Blind and Long-Term Studies," Journal of the American Geriatrics Society, vol. XXIV, No. 10, Oct. 1976, 440-446.
Davies et al., "Tolmetin Sodium and Indomethacin in the Treatment of Osteoarthrosis of the Hip: a Double-Blind Crossover Study," Current Medical Research and Opinion, vol. 7, No. 2, 1980, 115-120.
Liyanage et al., "Tolmetin in Osteoarthrosis of the Hip and Knee: Double-Blind Crossoever Trials," Current Medical Research and Opinion (1978) 5, 299-305.
Stacher, et al. "Effects of Tolmetin, Paracetamol, and of Two Combinations of Tolmetin and Paracetamol as Compared to Placebo on Experimentally Induced Pain. A Double Blind Study," International Journal of Clinical Pharmacology and Biopharmacy, vol. 17, No. 6, 1979, 250-255.

* cited by examiner

*Primary Examiner* — Marcos L Sznaidman
(74) *Attorney, Agent, or Firm* — Kilpatrick Townsend & Stockton LLP

(57) ABSTRACT

Provided herein are methods and compositions for controlling auxin responses in plants.

13 Claims, 8 Drawing Sheets

ANTI-AUXIN COMPOUNDS

CROSS-REFERENCES TO RELATED APPLICATIONS

This application claims the benefit of U.S. Provisional Application No. 62/218,439, filed Sep. 14, 2015, the entire specification and drawings are incorporated herein by reference.

BACKGROUND OF THE INVENTION

Plant hormones have been known and studied for years. Auxins, primarily indole-3-acetic acid (IAA) promote both cell division and cell elongation, and maintain apical dominance. Auxins also stimulate secondary growth in the vascular cambium, induce the formation of adventitious roots and promote fruit growth. Primary auxin activities are simulation of cell growth and elongation.

The most common naturally occurring auxin is indole-3-acetic acid (IAA). Synthetic auxins include indole-3-butyric acid (IBA); naphthalene acetic acid (NAA); 2,4-dichlorophenoxy acetic acid (2,4-D); and 2,4,5-trichlorophenoxy acetic acid (2,4,5-T or agent orange). Many of these synthetic auxins have been employed for decades as herbicides, producing accelerated and exaggerated plant growth followed by plant death.

Cytokinins, e.g., zeatin, are produced primarily in the roots of plants. Cytokinins stimulate growth of lateral buds lower on the stem, promote cell division and leaf expansion and retard plant aging. Cytokinins also enhance auxin levels by creating new growth from meristematic tissues in which auxins are synthesized.

The ratio of auxin to cytokinin can control differentiation of plant cells. Auxin is synthesized in the shoot apex, while cytokinin is synthesized mostly in the root apex. Thus, the ratio of auxin to cytokinin is normally high in the shoots, while it is low in the roots. If the ratio of auxin to cytokinin is altered by increasing the relative amount of auxin, root growth is stimulated. On the other hand, if the ratio of auxin to cytokinin is altered by increasing the relative amount of cytokinin, shoot growth is stimulated.

Plants require a certain ratio of auxin, e.g., IAA, to cytokinin for cell division. While the ratios may vary, the ratio of IAA to cytokinin must be much greater for cell division in the apical meristem tissue than the ratio in the meristem tissue of the roots. Each part of a plant may require a different IAA to cytokinin ratio for cell division. For example, different ratios may be required for cell division in the stem, fruit, grain and other plant parts. The ratio for apical meristem cell division may be considerably more, as much as 1000 times greater, than the ratio necessary for root cell division.

Shade is a key environmental cue that elicits rapid biosynthesis of auxin to promote elongated stem and petiole growth and accelerated reproduction (Tao et al. (2008) *Cell* 133:164). Inhibiting auxin perception can reduce shade-induced elongation of plant structures.

Auxin is also involved in plant resistance to insects and disease. In the 21-30° C. temperature range, plants produce sufficient amounts of auxins, particularly IAA, to maintain normal growth. Outside of these temperatures, auxin production declines for most plants, and microorganisms and insects are better able to multiply and feed on the plant. Pathogens can also exploit spatial auxin variations, e.g., those that can tolerate greater levels of IAA can attack the upper plant tissues, while those that require lower IAA levels attack the roots. By controlling the level of auxins in plant tissues, the ability of plants to resist attack by both pathogens and pests can be increased.

Auxin signaling is primarily mediated by three protein families: the AUXIN RESPONSE FACTOR (ARF) family of transcription factors that is responsible for the regulation of auxin-inducible gene expression, the auxin/indole-3-acetic acid (AUX/IAA) transcriptional inhibitors that interact with the ARFs and prevent their action, and F-box proteins that are part of the ubiquitin protein ligase $SCF^{TIR1}$ complex and control the rapid ubiquitin-mediated degradation of the AUX/IAA in response to auxin (Leyser (2006) *Curr. Biol.* 16:R424). TIR1 and related F-box proteins act as auxin receptors; binding of auxin strongly enhances their interaction with AUX/IAA and ultimately leads to degradation of AUX/IAA inhibitors (Dharmasiri et al. (2005) *Nature* 435:441; Kepinski & Leyser (2005) *Nature* 435:446).

Ethylene ($C_2H_4$) is a gaseous plant hormone that affects developmental processes and fitness responses in plants, such as germination, flower and leaf senescence, fruit ripening, leaf abscission, root nodulation, programmed cell death, and responsiveness to stress and pathogen attack (Johnson and Ecker (1998) *Annu Rev Genet.* 32, 227-254). Another effect of ethylene on plant growth is the so-called triple response of etiolated dicotyledoneous seedlings. This response is characterized by the inhibition of hypocotyl and root cell elongation, radial swelling of the hypocotyl, and exaggerated curvature of the apical hook.

Genetic screens based on the triple response phenotype have identified more than a dozen genes involved in the ethylene response in plants. Genetically-modified and naturally-occurring mutants in ethylene-related genes are commonly used in agriculture and commercially, as well as for study of plant processes. These mutants can be divided into categories: constitutive triple response mutants (e.g., eto1, eto2 and eto3, ctr1 and ran1/ctr2); ethylene insensitive mutants (e.g., etr1, etr2, ein2, ein3, ein4, ein5, and ein6); and tissue-specific ethylene insensitive mutants (e.g., hls1, eir1, and several auxin resistant mutants). Bleecker and Kende (2000) *Annu. Rev. Cell Dev. Biol.* 16:1 provides a review of ethylene signaling and loss-of-function mutants.

Ethylene and auxin signaling pathways are relatively well characterized. One interaction mode occurs at the hormone biosynthesis level: Auxin induces ethylene biosynthesis by upregulation of 1-aminocyclopropane-1-carboxylate (ACC) synthase, the key enzyme in ethylene production (Abel et al. (1995) *J. Biol. Chem.* 270:26020). Ethylene influences auxin levels by regulating the expression of two WEAK ETHYLENE INSENSITIVE (WEI2 and WEI7) genes that encode subunits of anthranilate synthase, a rate-limiting enzyme in Trp biosynthesis (Stepanova et al. (2005) *Plant Cell* 16:2230), from which pathway auxin is at least partially derived (Woodward & Bartel (2005) *Ann. Bot.* 95:707).

Synergistic effects of auxin and ethylene have been well defined in the regulation of hypocotyl elongation (Vandenbussche et al. (2003) *Plant Physiol.* 133:517), root hair growth and differentiation (Pitts et al. (1998) *Plant J.* 16:553), apical hook formation (Li et al. (2004) *Dev. Cell* 7:193), root gravitropism (Buer et al. (2006) *Plant Physiol.* 140:1384), and root growth (Rahman et al. (2001) *Plant Cell Physiol.* 42:301), showing that these two signaling pathways also interact at the molecular level. Auxin and ethylene also have synergistic effects on shade avoidance. In shade, auxin and ethylene biosynthesis rapidly increases. Moreover, exogenous ethylene escalates auxin biosynthesis and addition of auxin enhances ethylene production (Abel et al. (1995) *J. Biol. Chem.* 270:19093; Stepanova et al. (2005) *Plant Cell* 17:2230).

BRIEF SUMMARY OF THE INVENTION

Provided herein are compounds and compositions for modulating an auxin response in plants, preferably by inhibiting the response, wherein the compounds are represented in Formula I:

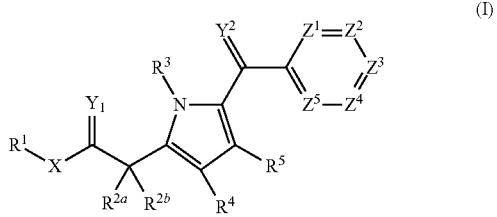

or a salt thereof, wherein:
each $R^1$ and $R^3$ is independently selected from the group containing hydrogen, alkyl, cycloalkyl, (cycloalkyl)alkyl, heterocycloalkyl, (heterocycloalkyl)alkyl, aryl, arylalkyl, heteroaryl, heteroarylalkyl, haloalkyl, perhaloalkyl, and heteroalkyl;
X is $N(R^1)$ or O;
each Y is independently O or S;
each Z (i.e., each of $Z^{1-5}$) is independently N or $C(R^6)$; and
each $R^2$, $R^4$, $R^5$, and $R^6$ is independently selected from the group containing hydrogen, alkyl, cycloalkyl, (cycloalkyl)alkyl, heterocycloalkyl, (heterocycloalkyl)alkyl, aryl, arylalkyl, heteroaryl, heteroarylalkyl, halo, haloalkyl, perhaloalkyl, heteroalkyl, $ZR^1$, and $N(R^1)_2$.

In some embodiments, $R^1$ is hydrogen, X is O, and each Y is O. In some embodiments, $R^{2a}$ and $R^{2b}$ are hydrogen. In some embodiments, $R^3$ is methyl. In some embodiments, $R^4$ and $R^5$ are hydrogen. In some embodiments, the —$CZ_5$ ring is a p-methylphenyl group.

In some embodiments, the compound of is tolmetin, as shown below, another acetic acid derivative of a nonsteroidal anti-inflamatory compound, or a salt thereof.

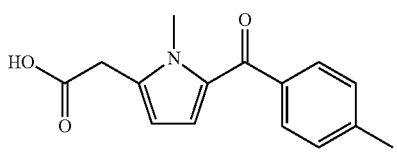 [SMILES: Cc1ccc(C(=O)c2ccc(CC(=O)O)n2C)cc1]

Further provided are agricultural compositions formulated for applying to a plant or plant part, comprising a compound of Formula I, as exemplified by tolmetin or a tolmetin salt. In some embodiments, the agricultural composition further comprises at least one of an herbicide, an herbicide safener, a surfactant, a fungicide, a pesticide, a nematicide, a plant activator, a synergist, a plant growth regulator, an insect repellant, an acaricide, a molluscicide, or a fertilizer.

Further provided are methods of inducing at least one auxin response in a plant, comprising contacting (or applying to) the plant an effective amount of a compound as described herein, e.g., in an agricultural composition, wherein the compound reduces the at least one auxin response in a control plant (e.g., an untreated control plant grown in similar conditions). In some embodiments, the compound reduces the at least one auxin response by at least 10, 20, 30, 40, 50, 60, 70, 80, 90, or 100% or more, e.g., as measured by size, length, or weight of a plant structure, or any other relevant auxin response phenotype. In some embodiments, the compound is applied at a concentration of 0.5-100 uM, 1-100 uM, 10-100 uM, 0.5-250 uM, 25-75 uM, 1 uM, 10 uM, 25 uM, 50 uM, 75 uM, 100 uM, 200 uM, or 500 uM. In some embodiments, the compound is applied more than once, e.g., at least 2, 3, 4, 5, 6, 7, 8, 9, or 10 times. In some embodiments, the compound is contacted with a plant part where the effect is desired.

In some embodiments, the compound is applied to a plant part (e.g., fruit, seed, bulb, leaf, shoot, flowering structure). In the case of contacting a plant part, one of skill will recognize that the plant part need not necessarily still be associated with the whole plant (e.g., a cutting, flower, seed, or bulb). In some embodiments, the plant is selected from the group of tomato, strawberry, tree fruit, avocado, wheat, rice, maize, or soy.

In some embodiments, the method further comprises detecting the auxin response in the plant. In some embodiments, the method further comprises harvesting the plant or part of the plant.

DETAILED DESCRIPTION OF THE INVENTION

Figure 1:
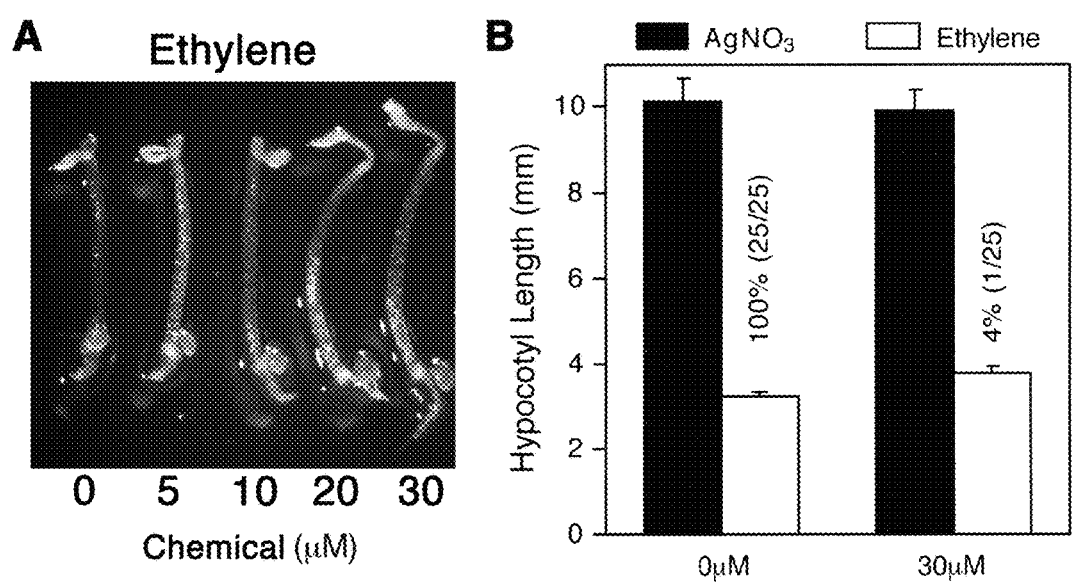
FIG. 1: Tolmetin (20-100 micromolar) partially blocks manifestation of the ethylene dependent seedling triple response, as evidenced by loss of apical hook formation in Col-0 wild type (wt) treated with saturating ethylene.

Provided herein is a new approach to controlling auxin and ethylene responses in plants. The compounds described herein, including tolmetin, can be used to inhibit auxin-dependent responses, and certain ethylene responses in a plant.

A. Definitions

An "agricultural composition" is a composition formulated for application to a plant or plant part (e.g., seed, cutting, shoots, etc.). An agricultural composition is typically in liquid form, e.g., for application by spraying or soaking, but can be in a powder for rehydration or application (dusting or dry coating), or gaseous form (e.g., for enclosed environments). The agricultural composition can be concentrated, e.g., for dilution or water or other solvent. An agricultural composition can also include more than one active ingredient, e.g., a compound of Formula I in combination with a fungicide, herbicide, fertilizer, etc.

The terms "auxin response," "auxin effect," etc., refers to any observable characteristic in a plant or plant part caused by auxin. Examples of auxin responses include, but are not limited to, floral patterning and development, fruit ripening, formation of vascular tissue, root growth (e.g., gravitropic response), phototropic growth and shade avoidance, apical hook formation, pest resistance, and fertility. The presently disclosed compounds "inhibit," "reduce," "interfere with," etc. auxin responses in plants. Auxin is also involved in ethylene biosynthesis, thus, the present compounds can also reduce ethylene responses. An agent or composition that reduces an auxin response in a plant typically reduces the auxin response of the plant at a given time, by at least 10%, 20%, 40%, 50%, 70%, 80%, 90% or more compared to control not treated with the agent or composition.

The terms "ethylene response," "ethylene effect," etc., refers to any observable characteristic in a plant or plant part caused by ethylene. Examples of ethylene responses include but are not limited to fruit ripening (e.g., climacteric fruit ripening), color development in citrus or other fruits, breaking seed or bulb dormancy, promotion of flowering (e.g., in orchard trees or ornamental plants), abscission (e.g., for crop harvest), controlling flower sex in cucurbits (see, e.g., Boualem et al. (2009) *PLoS ONE* 4:e6144), and pathogen resistance (e.g., to necrotrophic pathogens; see, e.g., van Loon et al. (2006) *Trends in Plant Sci.* 11:184). Ethylene responses also include inducing senescence and reducing growth. The presently disclosed compounds "inhibit," "reduce," "interfere with," etc. ethylene responses in plants, e.g., auxin-induced ethylene responses. An agent or composition that reduces an ethylene response in a plant typically reduces the ethylene response of the plant at a given time, by at least 10%, 20%, 40%, 50%, 70%, 80%, 90% or more compared to control not treated with the agent or composition.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a compound known to have the desired effect (positive control). A control can also represent an average value gathered from a number of tests or results. One of skill in the art will recognize that controls can be designed for assessment of any number of parameters. For example, a control can be devised to compare benefit, e.g., for peripheral composition considerations (e.g., half-life, adhesiveness) or for measures of the desired activity (e.g., comparison of pathogen resistance, growth, and/or side effects). Controls can be designed for in vitro applications, e.g., using a cell or tissue culture reporter gene assay. One of skill in the art will understand which controls are valuable in a given situation and be able to analyze data based on comparisons to control values. Controls are also valuable for determining the significance of data. For example, if values for a given parameter vary in controls, variation in test samples will not be considered as significant.

In the context of the present disclosure, examples of controls include use of mutant or transgenic plants with gain-of-function or loss-of-function in the auxin signaling or synthesis pathway. For example, to determine an effective amount for one of the compounds of Formula I for a given phenotype (e.g., reducing root development), controls can include a normal wild-type plant and a plant that lacks functional Cyp71B15 or AAO, involved in auxin biosynthesis, or a plant that lacks functional TIR1 or ARFs (auxin response factors), involved in auxin signaling. Another control can include a plant treated with an auxin biosynthesis inhibitor (e.g., aminoethoxyvinylglycine (AVG) or L-amino-oxyphenylpropionic acid (AOPP)).

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. Plants that can be treated as described herein include angiosperms (monocotyledonous and dicotyledonous plants), gymnosperms, ferns, horsetails, psilophytes, lycophytes, bryophytes, and multicellular algae.

The term "plant" also includes naturally-occurring mutants, genetically-modified plants, and transgenic plants.

A "genetically-modified plant" is one whose genome has been manipulated so that it is different than a wild-type plant of the same species, variety or cultivar, e.g., to add a gene or genetic element, remove a gene or genetic element, mutate a gene or genetic element, change chromatin structure, change RNA expression levels, etc. In the context of the present disclosure, genetically modified plants include but are not limited to those with a defect or mutation in an ethylene signaling pathway, e.g., in an ethylene receptor. Genetically-modified plants include transgenic plants.

A "transgenic plant" refers to a plant that contains genetic material not found in a wild-type plant of the same species, variety or cultivar. The genetic material can include a transgene, a reporter construct, an insertional mutagenesis event (such as by transposon or T-DNA insertional mutagenesis), an activation tagging sequence, a mutated sequence, a homologous recombination event or a sequence modified by chimeraplasty. A transgenic plant may contain an expression vector or cassette. The expression cassette typically comprises a polypeptide-encoding sequence or a modulating nucleic acid (e.g., an antisense, an siRNA or ribozyme) operably linked (i.e., under regulatory control of) to an appropriate inducible or constitutive regulatory sequences that allow for the expression of a polypeptide or modulating nucleic acid. The expression cassette can be introduced into a plant by transformation or by breeding after transformation of a parent plant. Such methods can be used in a whole plant, including seedlings and mature plants, as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec_butyl, tert_butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. "Arylalkyl" refers to a straight or branched, saturated, aliphatic radical having the number of carbon atoms indicated.

"Halogen" refers to fluorine, chlorine, bromine and iodine. "Halo" refers to the group including fluoro-, chloro-, bromo-, and iodo-.

"Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

The groups defined above can optionally be substituted by any suitable number and type of substituents. Representative substituents include, but are not limited to, halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen, unsubstituted alkyl, such as unsubstituted C$_{1-6}$ alkyl. Alternatively, R' and R", or R" and R'", when attached to the same nitrogen, are combined with the nitrogen to which they are attached to form a heterocycloalkyl or heteroaryl ring, as defined above.

"Salt" refers to acid or base salts of the presently described compounds. Illustrative examples of agriculturally acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the agriculturally acceptable salts are non-toxic. Additional information on suitable acceptable salts can be found in Remington's Pharmaceutical Sciences, 17th ed., Mack Publishing Company, Easton, Pa., 1985.

B. Plants

The presently described compounds can be effective for inducing an ethylene response in a broad range of plants, e.g., dicots or monocots and plants used for food, fiber, and fuel production. Exemplary plant species include but are not limited to species from the genera Asparagus, *Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. In some embodiments, the plant is an ornamental or flowering plant. In some embodiments, the plant is a vegetable- or fruit-producing plant, e.g., tomato, strawberry, fruit tree, etc.

Those of skill will recognize that a number of plant species can be used as models to predict the effects of the presently described compounds in other plants. For example, it is well recognized that tomato (*Solanum*) and *Arabidopsis* plants are useful models, e.g. for other dicots, and *Zea* can be a useful model for monocots in particular.

In some embodiments, the presently described compounds are used on mutant (e.g., naturally occurring or induced) or transgenic plants, e.g., auxin or ethylene gain-of-function mutants, mutants deficient in auxin or ethylene signaling pathways, or conditional mutants.

C. Compounds and Agricultural Compositions

Provided herein are compounds of Formula I that inhibit auxin responses in plants.

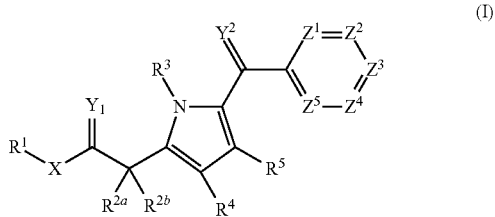

(I)

or a salt thereof, wherein:

each $R^1$ and $R^3$ is independently selected from the group containing hydrogen, alkyl, cycloalkyl, (cycloalkyl)alkyl, heterocycloalkyl, (heterocycloalkyl)alkyl, aryl, arylalkyl, heteroaryl, heteroarylalkyl, haloalkyl, perhaloalkyl, and heteroalkyl;

X is $N(R^1)$ or O;

each Y is independently O or S;

each Z ($Z^1$, $Z^2$, $Z^3$, $Z^4$, $Z^5$) is independently N or $C(R^6)$; and each $R^{2a}$, $R^{2b}$ $R^4$, $R^5$, and $R^6$ is independently selected from the group containing hydrogen, alkyl, cycloalkyl, (cycloalkyl)alkyl, heterocycloalkyl, (heterocycloalkyl)alkyl, aryl, arylalkyl, heteroaryl, heteroarylalkyl, halo, haloalkyl, perhaloalkyl, heteroalkyl, $ZR^1$, and $N(R^1)_2$.

In some embodiments, $R^1$ is hydrogen, X is O, and each Y is O. In some embodiments, $R^2$ is hydrogen. In some embodiments, $R^3$ is methyl. In some embodiments, $R^4$ and $R^5$ are hydrogen. In some embodiments, the —$CZ_5$ ring is a p-methylphenyl group.

In some embodiments, the compound of is tolmetin, as shown below, another acetic acid derivative of an NSAID, or a salt thereof

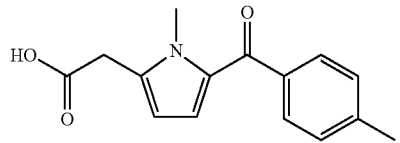 [SMILES: Cc1ccc(C(=O)c2ccc(CC(=O)O)n2C)cc1]

In some embodiments, the disclosure provides compositions for inhibiting at least one auxin response in a plant comprising an effective amount of at least one compound of Formula I (e.g., tolmetin or other acetic acid derivative of a nonsteroidal anti-inflammatory compound (NSAID)). In some embodiments, the application of the composition reduces the expression of an auxin responsive gene. "Effective amount" is intended to mean a compound or composition sufficient to reduce at least one auxin response, e.g., by 10%, 20%, 50%, 75%, 80%, 90%, 95%, or more compared to a negative control. In some embodiments, the effective amount of a compound of Formula I for reducing at least one auxin response is 0.05-250 uM, 0.1-200 uM, 0.1-100 uM, 0.5-100 uM, 10-100 uM, 5-50 uM, or 25-75 uM. A compound of the disclosure can be applied to a plant or plant part, e.g., to leaves or stems, or to soil, by methods known to those of ordinary skill in the art, including methods described herein.

An agricultural composition comprising a compound of Formula I can also include one or more of: a surface-active agent, an inert carrier, a preservative, a humectant, a feeding stimulant, an attractant, an encapsulating agent, a binder, an emulsifier, a dye, a UV protective, a buffer, a flow agent, a fertilizer, a nitrogen fixation agent, micronutrient donors, or other preparations that influence plant growth. The agricultural composition can also include one or more agrochemicals including: herbicides, insecticides, fungicides, bactericides, nematicides, molluscicides, acaracides, plant growth regulators, harvest aids, and fertilizers, which can also be combined with carriers, surfactants or adjuvants as appropriate for the agrochemical. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present disclosure are normally applied in the form of compositions and can be applied to the crop area, plant, or seed to be treated. For example, the compositions of the present disclosure may be applied during growth, seeding or storage.

Surface-active agents that can be used with the presently described compounds include anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials that can be used with the presently described compounds include, but are not limited to, inorganic minerals such as kaolin, phyllosilicates, carbonates, sulfates, phosphates, or botanical materials such as cork, powdered corncobs, peanut hulls, rice hulls, and walnut shells.

Herbicides that can be used with the presently described compounds include compounds that kill or inhibit growth or replication of plants, typically a subset of plants that is distinct from the desired plant or crop. There are several modes of action: ACCase inhibition, carotenoid biosynthesis inhibition, cell wall synthesis inhibition, ALS inhibition, ESP synthase inhibition, glutamine synthase inhibition, HPPD inhibition, microtubule assembly inhibition, PPO inhibition, etc. Examples of commercially available herbicides include One-Time®, MSMA, Corvus®, Volunteer®, Escalade®, Q4®, Raptor®, Acumen®, Sencor®, Bullet®, TopNotch®, Valor®, PastureGard®, glycophosate (Roundup®), DSMA, Break-Up®, Hyvar®, Barricade®, etc. Herbicides can be mixed with "herbicide safeners" to reduce general toxicity of the herbicide, as described, e.g., in Riechers et al. (2010) *Plant Physiol.* 153:3.

Pesticides (e.g., nematicides, molluscicides, insecticides, miticide/acaricides) can be used in combination with the presently disclosed compounds to kill or reduce the population of undesirable pests affecting the plant. Pesticides can also be used with repellants or pheromones to disrupt mating behavior. Insecticides are directed to insects, and include, e.g., those of botanical origin (e.g., allicin, nicotine, oxymatrine, jasmolin I and II, quassia, rhodojaponin III, and limonene), carbamate insecticides (e.g., carbaryl, carbofuran, carbosulfan, oxamyl, nitrilacarb, CPMC, EMPC, fenobucarb), fluorine insecticides, formamidine insecticides, fumigants (e.g., ethylene oxide, methyl bromide, carbon disulfide), chitin synthesis inhibitors, macrocyclic lactone insecticides, neonicotinoid insecticides, organophosphate insecticides, urea and thiourea insecticides, etc. Nematicides affect nematodes, and include, e.g., organophosphorus nematicides (e.g., diamidafos, fosthiazate, heterophos, phsphamidon, triazophos), fumigant nematicides (e.g., carbon disulfide, methyl bromide, methyl iodide), abamectin, carvacrol, carbamate nematicides (e.g., benomyl, oxamyl), etc. Molluscicides are directed to slugs and snails, and include, e.g., allicin, bromoacetamide, thiocarb, trifenmorph, fentin, copper sulfate, etc. Many pesticides target more than one type of pest, so that one or two can be selected to target insects, mollusks, nematodes, mitogens, etc.

Fertilizers typically provide macro- and micronutrients in a form that they can be utilized by the plant, or a plant-associated organism. These include, e.g., nitrogen, phosphorus, potassium, sulfur, calcium, potassium, boron, chlorine, copper, iron, manganese, molybdenum, zinc, nickel, and selenium. Fertilizers are often tailored to specific soil conditions or for particular crops or plants. Fertilizers that can be used with the presently described compounds include naturally-occurring, modified, concentrated and/or chemically synthesized materials, e.g., manure, bone meal, compost, fish meal, wood chips, etc., or can be chemically synthesized, UAN, anhydrous ammonium nitrate, urea, potash, etc. Suppliers include Scott®, SureCrop®, BCF®, RVR®, Gardenline®, and many others known in the art.

Fungicides are compounds that can kill fungi or inhibit fungal growth or replication. Fungicides that can be used with the presently disclosed compounds include contact, translaminar, and systemic fungicides. Examples include sulfur, neem oil, rosemary oil, jojoba, tea tree oil, *Bacillus subtilis*, Ulocladium, cinnamaldehyde, etc.

The compositions of the disclosure can be in a suitable form for direct application or as a concentrate of primary composition that requires dilution with a suitable quantity of water or other diluent before application. The concentration of a compound of Formula I will vary depending upon the nature of the particular formulation, specifically, whether it is a concentrate or to be used directly, the type of plant, and in some cases, on the nature of the use, e.g., for controlling lodging in cereal crops or inhibiting regreening of citrus.

D. Methods of Determining Auxin and Ethylene Responses

Auxin responses can be assayed by detecting expression of any of a number of auxin responsive genes (e.g., DH5, AtHB20, AtHB8, IAA1, IAA19, GH3 genes). See, e.g., Mattsson et al. (2003) *Plant Physiol.* 131:1327. This can be accomplished using standard methods, e.g., by detecting a reporter gene such as GUS or GFP, or by directly detecting an mRNA or protein gene product, e.g., using a Northern or Western blot.

Phenotypes of reduced auxin response include disrupted floral patterning and delayed or reduced floral organ number, reduced vascular tissue formation and root growth, reduced gravitropic and phototropic responses, elongated hypocotyls, and at least partial sterility.

Ethylene responses can be conveniently assayed using a number of standard assays, and is commonly determined by observing the "triple response" phenotype. Upon exposure to ethylene, wild type plants show radial expansion of the hypocotyl, inhibition of root and hypocotyl elongation, and exaggeration of the apical hook (Neljubow (1901), Pflanzen Beih. Bot. Zentralbl., 10:128-139). Mutants that cause constitutive ethylene signaling are characterized by a reduced stature compared to wild type plants (Guzman and Ecker (1990) *Plant Cell* 2:513-523; Kieber et al. (1993) *Cell* 72:427-441). Mutants that are insensitive to ethylene do not display the triple response upon exposure to ethylene, and often have hypocotyl and root lengths and apical structures that are about the same before and after ethylene exposure.

Dark-induced senescence assays can be used. Such assays typically involve sheathing leaves while still attached to the plant for one week. The lack of light induces leaf senescence, which can be delayed in ethylene insensitive plants, or plants grown in low/substantially absent ethylene.

Ethylene insensitive plants, or plants grown in low/substantially absent ethylene are typically larger, even when compared to wild type plants grown under optimal conditions, i.e., in the absence of trace levels of ethylene that may accumulate in enclosed growth facilities. However, it will be recognized by those with skill in the art that ethylene responses vary according to plant species and environmental conditions. Examples of ethylene signaling assays are provided in Alonso et al. (2003) *PNAS* 100:2992 and van Loon et al. (2006) *Trends in Plant Sci.* 11:184.

E. Methods of Treating

The presently described compounds can be applied to the environment of a plant or plant structure by, for example, spraying, atomizing, dusting, scattering, coating or pouring, introducing into or on the soil, introducing into irrigation water, by seed treatment or general application or dusting at the time that inhibition of a particular auxin or ethylene response is desired.

The presently described compounds can be applied simultaneously or in succession with other compounds. Methods of applying an active ingredient or agricultural composition of the present disclosure that contains at least one compound of Formula I include, but are not limited to, foliar application (e.g., spray or soak), application to fruit or flowering structures, seed coating, and soil application. The number of applications and the rate of application depend on desired use, e.g., reducing plant mass or preventing citrus regreening, and conditions, e.g., the size of the plant, temperature, moisture, etc.

F. Applications

The presently described compounds can be used to treat plants to regulate the timing of auxin and ethylene responses, e.g., inhibiting hypocotyl elongation, root development and growth, apical hook formation, shade avoidance, floral development, fruit ripening, etc. until a desired time. The compounds of Formula I can be used to reduce ethylene production in a plant or plant part, thereby inhibiting ethylene responses. The compounds of Formula I can be applied to maintain immature plants or plant parts (e.g., a plant cutting) during transport or storage. In some embodiments, the compounds of Formula I can be used to delay fruit ripening, e.g., until weather or other environment conditions improve or during transport or storage, or to reduce regreening of citrus. The compounds can also be used to reduce plant resistance to certain infective vectors, e.g., transgenic or recombinant viral, bacterial, or fungal vectors. The compounds of Formula I can be used to thin foliage and flowers for easier fruit harvest. The compounds of Formula I can be used to prevent lodging in a cereal crop (e.g., wheat, barley, oats, etc.).

EXAMPLES

A chemical library screen was conducted to identify chemicals capable of preventing manifestation of the ethylene-regulated seedling triple response in the *Arabidopsis* constitutive ethylene response mutant, ctr1. From this screen, Pamoic acid (PA) and Tolmetin were found to prevent apical hook formation in both ctr1-3 and ethylene-treated Col-0 wt. Structural analyses of PA and Tolmetin revealed that both have features of auxin-like molecules, suggesting that each acts as an anti-auxinic compound that blocks auxin-regulated ethylene responses in plants. Further analysis of the growth effects of each chemical demonstrated that they prevent several auxin-related phenomena including auxin-dependent root growth inhibition, positive root gravitropism, induction of the auxin responsive DR5::GUS reporter, and modulation of ethylene-dependent gene expression. Our results suggest that PA and Tolmetin function as anti-auxins potentially at the level of the auxin receptors and that auxin in part acts to control the magnitude of ethylene response, with loss of auxin signaling leading to reduced ethylene response.

Introduction

Ethylene is a key plant hormone that controls development and progression of several agriculturally important phenomena (Abeles et al., 1992). While substantial gains in knowledge have been made regarding how ethylene signaling occurs, gaps in our understanding continue to exist including regulation of the level of ethylene response by auxin and brassinosteroids (Deslauriers and Larsen, 2010; Robles et al., 2012; Stepanova and Alonso, 2009). Through isolation of *Arabidopsis* mutants with altered ethylene response, several biochemical factors responsible for ethylene binding and signal transmission have been identified. Ethylene signaling initiates through binding of this simplest unsaturated hydrocarbon to a family of five endoplasmic reticulum localized ethylene receptors (Hua and Meyerowitz, 1998). In the absence of ethylene, the receptors are responsible for maintaining CTR1, which is a MAPKKK-like protein that negatively regulates the pathway, in an active state (Kieber et al., 1993). After ethylene binding, CTR1 stops phosphorylating it's downstream target, EIN2, resulting in EIN2's C-terminus being cleaved and transiting into the nucleus (Ju et al., 2012; Qiao et al., 2012; Wen et al., 2012). As part of this response, two master transcription factors, EIN3 and EIL1 (Alonso et al., 2003; Chao et al., 1997), which normally are at very low levels due to proteolytic turnover (Binder et al., 2007; Gagne et al., 2004; Guo and Ecker, 2003; Potuschak et al., 2003), accumulate and activate ethylene dependent transcription.

Several inhibitors that control ethylene-dependent phenomena have been identified, with these being categorized into those that prevent ethylene biosynthesis or ethylene signaling. Ethylene biosynthesis is a simple two-step catalytic process (Abeles et al., 1992; Bleecker and Kende, 2000) in which the general methyl donor S-adenosylmethionine is converted into 1-aminocyclopropane-1-carboxylic acid (ACC) by a family of enzymes commonly known as ACC synthase (ACS). ACC is subsequently broken down by ACC oxidase (ACO) to form ethylene. Inhibitors of both steps have been identified, including aminoethoxyvinylglycine for ACS and aminooxyacetic acid for ACO (Abeles et al., 1992). A second group of chemicals that block ethylene phenomena are responsible for inhibiting the ethylene response pathway by preventing ethylene binding or action at the receptors. Chemicals in this group include unsaturated bulky hydrocarbons such as Norbornadiene and 1-Methylcyclopropene (Sisler, 2006), which compete with ethylene for binding to the $Cu^{2+}$ moiety in the ethylene-binding pocket (Rodriguez et al., 1999). $Ag^{2+}$ can substitute for $Cu^{2+}$ in the ethylene-binding pocket and, even though it still allows ethylene binding, prevents ethylene from activating signaling (McDaniel and Binder, 2012; Rodriguez et al., 1999).

Materials and Methods

Growth Conditions

For screening for chemicals that reduce ethylene response, *Arabidopsis* ctr1-3 seeds were planted on a microtiter plate containing PNS media in the presence of individual chemicals (50 µM concentration of each) from the Microsource Spectrum Collection. Seedlings were grown in the dark for 4 d after which they were scored for manifestation of the ethylene responsive triple response. For all other growth experiments, seedlings were planted on PNS media supplemented with the relevant chemical (Deslauriers and Larsen, 2010). For conditions requiring pamoic acid, media was supplemented with Pamoic acid disodium salt (Sigma Life Science, St. Louis, Mo.). Measurement of ethylene production was conducted as previously described (Deslauriers and Larsen, 2010).

Northern Analysis

Total RNA was extracted from leaf tissue using the RNeasy Plant Mini Kit (Qiagen, Valencia, Calif.). 10 μg of total RNA was separated by electrophoresis in a 1% (w/v) denaturing agarose gel, after which the RNA was blotted to Zeta-Probe GT Blotting Membrane (Bio-Rad, Hercules, Calif.). $^{32}$P-labelled probes were generated using the RadPrime DNA labeling system (Invitrogen).

GUS Analysis

GUS analysis of DR5::GUS lines was performed as previously described (Ni et al., 2001).

Molecular Docking

The crystal structure of the TIR1/auxin complex (PDB ID: 2P1P) was chosen as a starting model for molecular docking using Vina software (Trott and Olson, 2010). The Pamoic acid structure was derived from a small molecule crystal structure (Haynes et al., 2005; Cambridge structure database reference code: JAWYAI). For docking calculations the default parameters were used. However, the side chains of residues F82 and R403 of the TIR1 receptor were set as flexible with the rest of the receptor being kept rigid. The visualization and comparison of the docking results with the crystal structure of TIR1-auxin-IAA7 (Tan et al., 2007; RCSB protein data bank extension: 2P1Q) were performed with COOT (Emsley and Cowtan, 2004). The final images of the structural comparison were prepared with PyMOL [The PyMOL Molecular Graphics System, Version 1.5.0.4 Schrödinger, LLC] and Adobe Illustrator CS5 (www.adobe.com).

Results

Identification of Chemicals that Block Ethylene Response

A chemical library screen was performed in which etiolated seedlings of the constitutive ethylene response mutant, ctr1-3, were grown in air for 4 d in the presence of chemicals from the Microsource Spectrum Collection, a bioactive and natural compound library consisting of 2000 different compounds. ctr1-3 seedlings were scored for presentation of the ethylene regulated seedling triple response, consisting of severe hypocotyl and root shortening and exaggerated apical hook formation. Three chemicals were identified that blocked apical hook formation and resulted in measurably longer roots. These included Hydroxyzine pamoate, Pyrantel pamoate, and Tolmetin.

Figure 2:
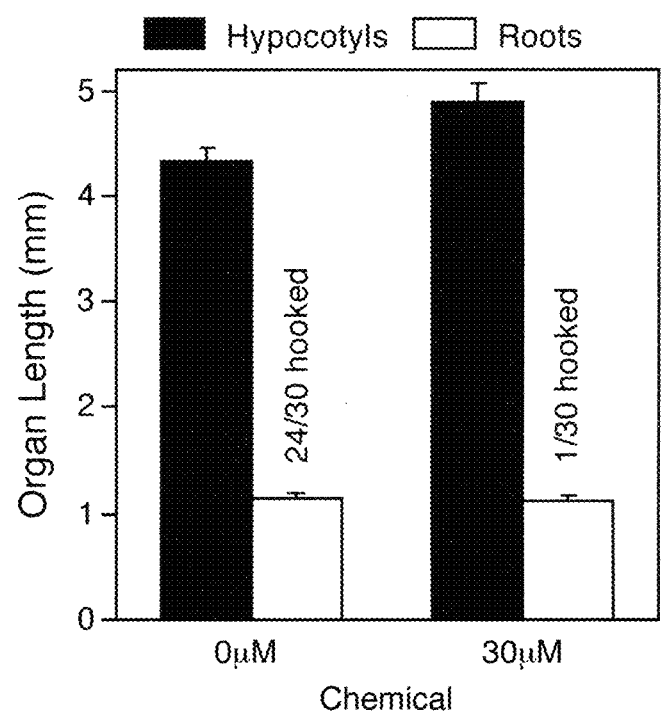
FIG. 2: Tolmetin partially blocks ethylene responses in an *Arabidopsis* mutant that has a constitutive ethylene response. Dark grown ctr1-3 seedlings have nearly complete loss of apical hook formation at 30 micromolar Tolmetin. Tolmetin does not affect ethylene-dependent root growth inhibition at this concentration.

Subsequent analysis of the cationic partner of the first two compounds did not lead to blockage of the seedling triple response in ctr1-3. Pamoic acid (PA), which is the anionic partner of both of the first two substances, was subsequently found to prevent presentation of ethylene dependent phenomena. Ethylene treated Col-0 wt and air grown ctr1-3 etiolated seedlings were tested for manifestation of the seedling triple response following treatment with PA or Tolmetin. For Col-0 wt, seedlings were grown in either the presence or absence of 5 μM AgNO$_3$, an inhibitor of ethylene perception, or 100 μL L$^{-1}$ ethylene, which is a concentration that results in maximal response in etiolated seedlings. Additionally, the two treatments were exposed to either 0 or 10 μM PA or a range of Tolmetin concentrations up to 30 μM (FIG. 1). After 4 d growth in the dark, seedlings were examined to determine whether PA or Tolmetin treatment blocks aspects of the ethylene dependent triple response. Col-0 wt seedlings treated with AgNO$_3$ and PA were shorter than those not treated with PA, indicating that PA has undefined inhibitory effects on growth independent of ethylene (FIGS. 1-2). This negative effect was not seen for Tolmetin treated Col-0 wt seedlings (FIG. 2). Analysis of Col-0 wt seedlings exposed to saturating ethylene revealed that PA blocks ethylene dependent phenomena in both roots and hypocotyls, with seedlings treated with ethylene and PA having measurably longer roots and complete loss of apical hook formation compared to those that were not treated with PA. In contrast, the effects of Tolmetin are specific to hypocotyls of ethylene treated Col-0 wt, resulting in nearly complete loss of apical hook formation in the presence of ethylene (FIG. 1). It should be noted that the phenotype of PA-treated seedlings in the presence of saturating ethylene is strikingly similar to ethylene-treated wei8 and tart loss-of-function mutants, which are deficient in auxin biosynthesis (Stepanova et al., 2008).

Figure 3:
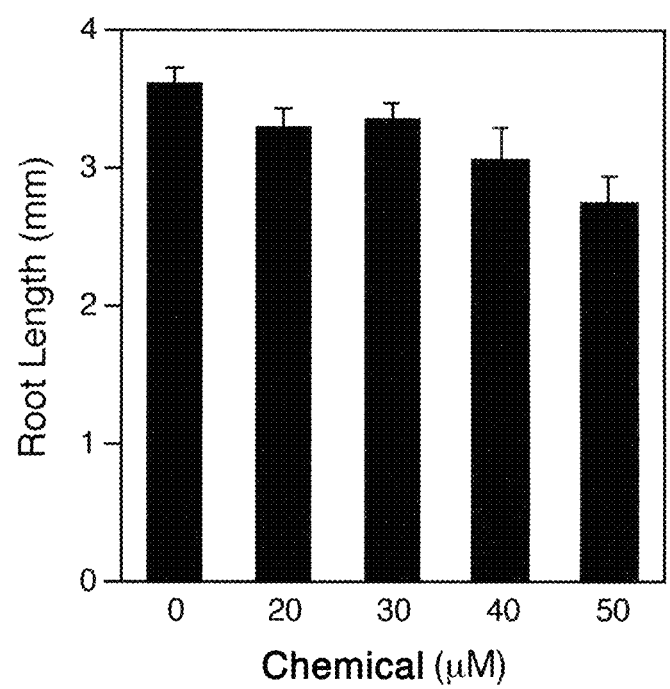
FIG. 3. Tolmetin does not block ethylene dependent root growth inhibition. Seedlings of the constitutive ethylene response mutant ctr1-3 were grown in the light in the presence of increasing concentrations of Tolmetin. No positive effect on root growth was observed for Tolmetin treated ctr1-3 seedlings.
Figure 4:
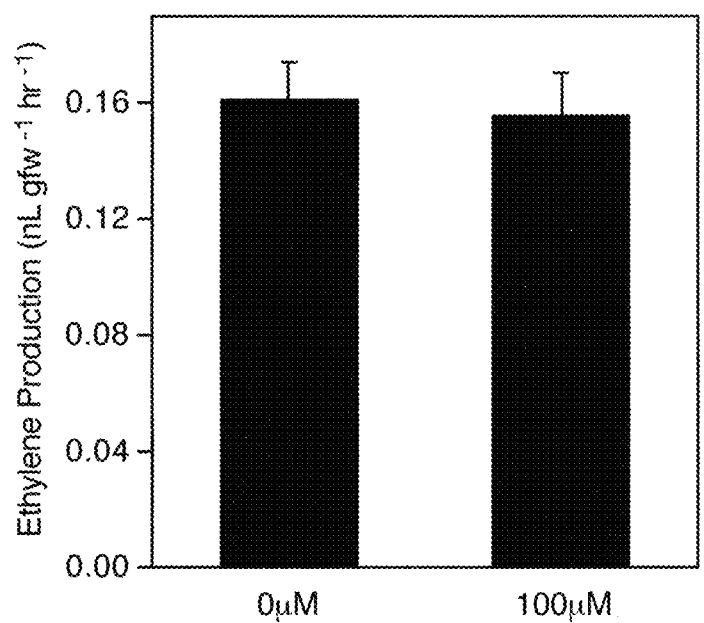
FIG. 4. Tolmetin does not reduce ethylene biosynthesis. Col-0 wt seedlings were grown in the dark for 4 days in the absence or presence of 50 micromolar Tolmetin, after which ethylene biosynthesis was measured. Any inhibition of ethylene dependent responses by Tolmetin is not related to reduced ethylene biosynthesis.

It was then determined what effect PA and Tolmetin had on the constitutive ethylene response mutant, ctr1-3. Addition of as little as 10 μM PA or 30 μM Tolmetin fully eliminated apical hook formation in the ctr1-3 mutant compared to the untreated control (FIG. 2), with the hypocotyls of PA- or Tolmetin-treated ctr1-3 being nearly identical to ctr1-1; tar2-1; wei8-1 (Stepanova et al., 2008). Growth of ctr1-3 seedlings in the presence of 10 μM PA substantially alleviated the severe root growth inhibition seen for this constitutive triple response mutant, which is consistent with PA opposing ethylene response (FIG. 3). As for ethylene treated Col-0 wt, treatment with Tolmetin did not prevent the severe root growth inhibition seen for ctr1-3 (FIG. 3). Similar effects on ethylene related phenomena were seen following application of PA to light grown ctr1-3 seedlings, with PA treated ctr1-3 seedlings being morphologically indistinguishable from wt. The effects seen for PA-treated and Tolmetin-treated ctr1-3 are consistent with PA and Tolmetin functioning as anti-ethylene compounds that target one or more biochemical mechanisms at or below CTR1.

PA and Tolmetin Treatments do not Reduce Ethylene Biosynthesis

Even though PA and Tolmetin are capable of reversing the ctr1-3 constitutive triple response phenotype and limiting ethylene response in Col-0 wt treated with saturating ethylene, it was necessary to show that PA and Tolmetin act to block ethylene response rather than ethylene biosynthesis. In order to demonstrate this, etiolated Col-0 wt seedlings were grown in the absence or presence of either 10 μM PA or 30 μM Tolmetin for 96 h after which levels of ethylene generated in the last 18 h of the growth period were measured using gas chromatography. As shown in FIG. 2, treatment with either PA or Tolmetin had no measurable effect on ethylene biosynthesis, which is consistent with PA and Tolmetin acting as inhibitors of ethylene response rather than ethylene production.

PA Treatment Elevates Ethylene Responsive Gene Expression

Manifestation of ethylene response is dependent on transcriptional induction of ethylene-regulated genes (Alonso et al., 2003; Chao et al., 1997; Solano et al., 1998). This relies on two primary transcription factors, EIN3 and EIL1, with mutational loss of both causing nearly complete ethylene insensitivity. It could be predicted that since PA treatment limits ethylene response it would also reduce or prevent ethylene inducible gene expression similar to the ethylene insensitive ein3-1; eil1-1 double mutant. To test this, Col-0 wt seedlings were treated with 5 μM AgNO$_3$ or increasing concentrations of ethylene in the absence or presence of 25 μM PA, which is also a concentration that results in blockage of ethylene response. Rather than reduce expression of a subset of ethylene responsive genes, PA treatment had a negligible effect on ETR2 expression and caused hyperinduction of two other genes, AtEBP and ACO2. The latter two genes are not properly expressed in a group of enhanced ethylene response Arabidopsis mutants, with these argued to be members of a subset of ethylene regulated genes whose products are required for controlling the magnitude of ethylene response (Christians and Larsen, 2007; Christians et al., 2008; Deslauriers and Larsen, 2010; Robles et al., 2007).

In contrast to PA treatment, auxin has an antagonistic relationship regarding induction of this same subset of genes. Col-0 wt seedlings were grown hydroponically in the dark for 4 d in the presence of 5 µM $AgNO_3$, 1 µM ACC or 10 µM ACC in the absence or presence of 10 µM 1-naphthaleneacetic acid (NAA) after which tissue was collected for RNA isolation and Northern analysis. Whereas both ACO2 and AtEBP show normal ethylene responsive induction following treatment with ACC, supplementation of each treatment with NAA nearly eliminated induction of each. In contrast, treatment with NAA had no obvious effect on ETR2 expression. From these results, auxin likely regulates the level of ethylene response in a manner correlated with expression of the subset of genes that have previously been linked to control of the magnitude of ethylene response, with auxin increasing the level of ethylene response in conjunction with reducing expression of these genes.

PA Blocks Auxin Dependent Enhancement of Ethylene Inducible Gene Expression

It was found that PA treatment prevented induction of ethylene regulated defense genes in Arabidopsis leaves. For this analysis, Arabidopsis plants were grown hydroponically for 13 d after which they were treated with or without 10 µM ACC in the absence or presence of 25 µM PA, with all samples exposed to 10 µM+/−JA for the 24 h treatment period. Treatment with ACC resulted in increased expression of both chiB and PDF1.2. Auxin functions in a synergistic manner with ethylene and JA to control expression of PDF1.2, with addition of auxin resulting in its hyperinduction (Robles et al., 2012). This was also found in our experimental setup in which supplementation of the 10 µM ACC treatment with 250 nM NAA resulted in chiB and PDF1.2 levels that were far greater than what was observed following treatment with ACC alone. Addition of PA to ACC treated rosettes caused a sharp decrease in expression of both chiB and PDF1.2 even in the presence of exogenous auxin.

PA Reverses the Sar1-7 Enhanced Ethylene Response Phenotype

A previously identified mutant with increased auxin response, sar1-7, also has enhanced ethylene response (Robles et al., 2012). Based on results with sar1-7, it was concluded that auxin conditions ethylene response, with auxin hypersensitivity in this mutant resulting in increased ethylene response. Because of this relationship and the effect of PA on auxin-dependent enhancement of ethylene inducible gene expression, it was determined whether PA could reverse the ethylene hypersensitivity seen for etiolated sar1-7 seedlings. Seedlings of Ws wt and sar1-7 were grown for 4 d in the dark in the presence of either 5 µM $AgNO_3$ or 100 µL $L^{-1}$ ethylene with or without 30 µM PA. Whereas treatment of sar1-7 with saturating ethylene leads to greater than wt inhibition of hypocotyl elongation, addition of PA results in substantial reversal of the ethylene hypersensitivity phenotype seen for the mutant, which is similar to what was observed following treatment with an anti-auxin, p-Chlorophenoxyisobutyric acid (PUB) (Robles et al., 2012).

As discussed previously, enhanced ethylene response can be correlated with loss of expression of the aforementioned group of genes that have been proposed to regulate the magnitude of response, including AtEBP. Northern analysis of ethylene treated etiolated seedlings of Ws wt and sar1-7 revealed that consistent with what has been reported for other eer mutants, ethylene treated sar1-7 seedlings have reduced expression of AtEBP compared to Ws wt. This suggests that loss of AtEBP expression along with other unidentified members of this subset of genes and the concomitant ethylene hypersensitivity in this mutant may arise from increased auxin responsiveness in sar1-7. Consistent with this model, addition of PA to Ws wt and sar1-7 seedlings resulted in hyperexpression of AtEBP and ACO2, but not ETR2, in the presence of saturating ethylene.

PA and Tolmetin are Structurally Similar to NAA and IAA Respectively

Based on the effects that PA has on auxin-dependent regulation of ethylene responsive gene expression, the strong similarity between PA treatment and the phenotypes of tar2-1; wei8-1 and L-kynurenine treated ctr1-1 seedlings following ethylene exposure (He et al., 2011; Stepanova et al., 2008), and the reversal of the auxin dependent ethylene hypersensitivity phenotype of sar1-7, it seemed that PA could be reducing ethylene response by blocking auxin signaling. This model was particularly compelling after comparison of the structure of PA to the synthetic auxin NAA. PA shares many structural similarities with NAA and is highly reminiscent of two NAA molecules covalently linked by a single carbon bridge. It should also be noted that the structure of Tolmetin has similarities to that of IAA, suggesting that it also may be capable of blocking auxin signaling possibly through competitive inhibition. Based on these comparisons, it could be argued that PA or Tolmetin could fit within the auxin binding pocket of one or more of the auxin receptors, with these molecules likely blocking assembly of protein complexes necessary for promotion of auxin responses. Since auxin signaling controls ethylene response in an unknown manner, it could be hypothesized that PA and Tolmetin block ethylene responses through inhibition of auxin signaling.

PA and Tolmetin Block Auxin-Dependent Phenomena in Arabidopsis

Auxin is required for normal root growth since at physiological concentrations it promotes cell elongation. Because of this, it was examined whether PA or Tolmetin inhibit root growth, which would be consistent for molecules that block auxin action. Col-0 wt seedlings were grown in the absence or presence of increasing concentrations of PA or Tolmetin for 7 d after which root length was measured. Addition of increasing concentrations of PA or Tolmetin led to severe inhibition of root length compared to untreated control roots. These results could be interpreted as resulting from PA and Tolmetin blocking auxin-dependent promotion of root growth. At low concentrations of both PA and Tolmetin, there is actually a stimulatory effect of each chemical on root growth that is consistent with hormesis. Since auxin is inhibitory to growth at higher concentrations even though it is required for growth at physiological levels, this result could be interpreted as each chemical relieving the negative effects of auxin at low concentrations, with the severe growth inhibition seen for high concentrations resulting from complete blockage of all auxin effects including those associated with promotion of growth.

Figure 5:
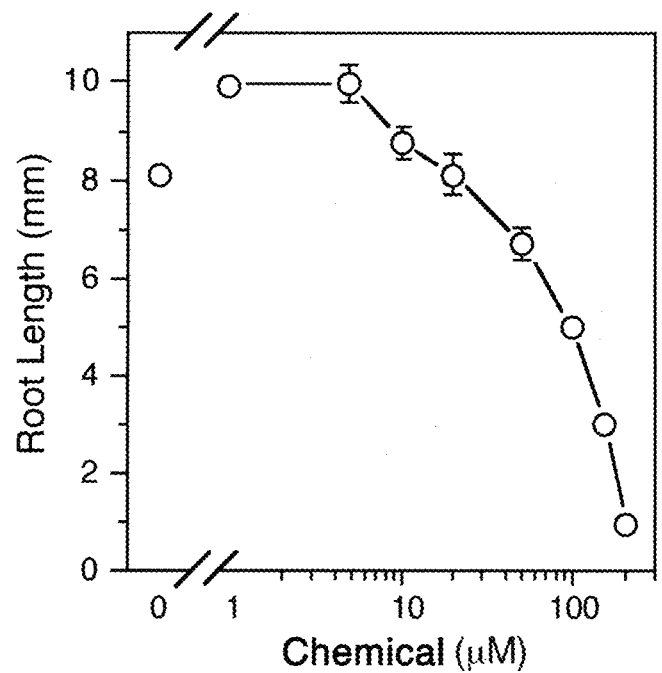
FIG. 5. Tolmetin is inhibitory to root growth at high concentrations. Seedlings were grown in the light in the presence of increasing concentrations of Tolmetin for 5 days after which root length was measured. Based on the characteristics of this dose response analysis, Tolmetin likely blocks auxin response, since auxin is required for normal root growth.

Addition of as little as 50 nM of various auxins such as IAA or NAA can significantly reduce root growth, likely due to internal auxin concentrations being pushed to a level that is beyond the optimum for promoting root elongation. Consequently, it was assessed whether PA or Tolmetin treatment blocked the inhibitory effects of exogenously added auxin. It was determined that 30 µM PA and 50 µM Tolmetin would be the best concentrations to use for this experiment since these concentrations would likely be inhibitory to auxin dependent effects yet would not be so severe as to completely block root growth. Col-0 wt seedlings were grown in the light in the absence or presence of 150 nM NAA with or without 30 µM PA or in the absence or presence of 300 nM IAA with or without 50 µM Tolmetin. After 7 d growth, root length was measured for all samples. Treatment with either NAA or IAA caused severe root growth inhibition compared to untreated roots (FIG. 5). In contrast, even though roots were significantly inhibited when treated with PA or Tolmetin alone compared to untreated roots, treatment with either PA or Tolmetin greatly reduced the inhibitory effects of exogenous auxin.

Figure 6:
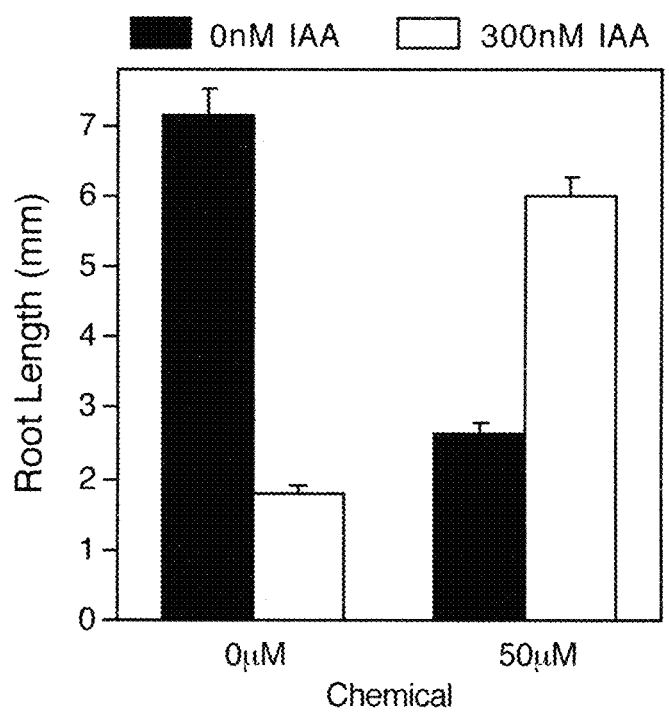
FIG. 6. Tolmetin blocks auxin dependent inhibition of root growth. Col-0 wt seedlings were grown for 5 days in the absence or presence of 50 micromolar Tolmetin supplemented with either 0 or 300 nM IAA (indole-3-acetic acid, a major auxin), after which root length was measured. Treatment with 50 micromolar Tolmetin resulted in significant root growth inhibition. The inhibitory effect of Tolmetin was almost completely overcome with addition of 300 nM IAA, which was severely inhibitory to roots in the absence of Tolmetin. These results demonstrate that the inhibitory effect of auxin depends on blockage of auxin perception. Tolmetin is an anti-auxin that among other things blocks the effects of auxin on ethylene signaling.
Figure 7:
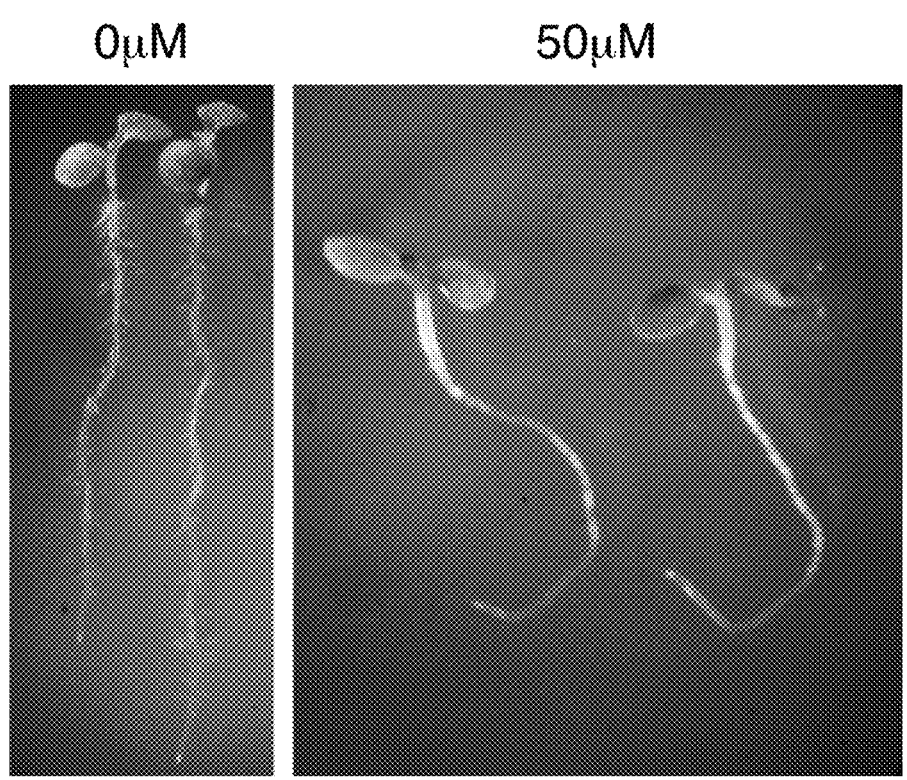
FIG. 7. Tolmetin blocks gravitropism in light grown roots. Col-0 wt seedlings were grown for 5 days in the light in the absence or presence of 50 micromolar Tolmetin. Untreated roots grew with gravity in a downward direction. Tolmetin treated roots completely lacked root hairs (production of which is auxin dependent) and showed agravitropic root growth consistent with blockage of auxin signaling.

Since normal auxin signaling is required for proper gravitropic responses in roots, it was determined whether treatment with either PA or Tolmetin would result in agravitropic root growth. Col-0 wt seedlings were grown for 4 d on vertical agar plates either in the absence or presence of 30 µM PA or 50 µM Tolmetin, after which root growth was assessed. Whereas untreated seedlings uniformly grew downward, PA- and Tolmetin-treated roots grew in a random manner that was independent of gravity with most seedlings showing upward root growth (FIG. 6).

Figure 8:
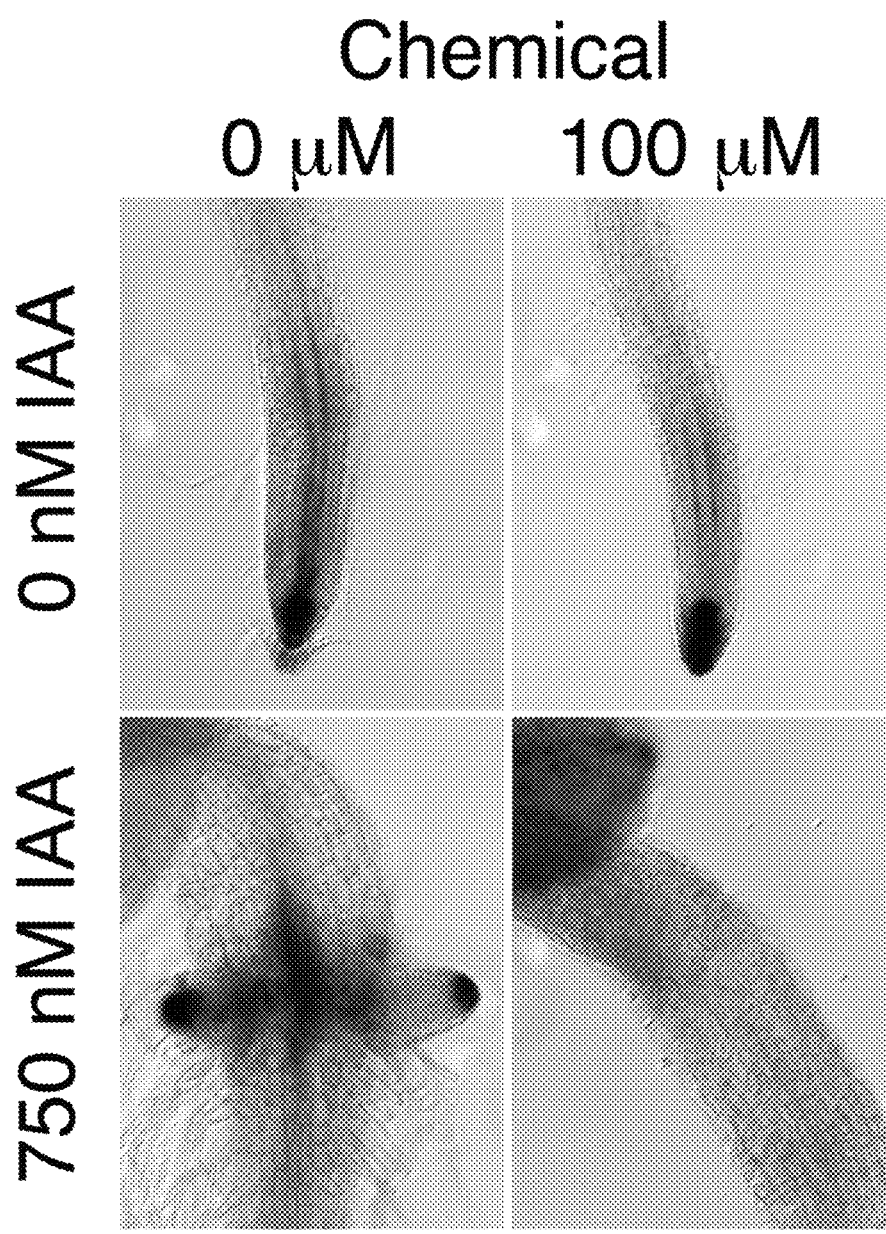
FIG. 8. Tolmetin blocks auxin inducible gene expression in Col-0 DR5::GUS seedlings. DR5::GUS seedlings have been used to monitor the effect of auxin on gene expression since the GUS reporter gene is under the control of auxin responsive promoter elements in this transgenic line. Development of dark color shows areas that are responding to auxin (auxin-dependent gene expression). In the absence of exogenous auxin, there is a comparable level of dark color in both the 0 and 100 micromolar Tolmetin samples, demonstrating that endogenous auxin levels are similar and Tolmetin does not block endogenous auxin biosynthesis. In contrast, addition of 750 nM IAA promotes initiation of lateral roots as demonstrated by dark stained secondary roots emerging from the root shoot junction. Treatment with Tolmetin completely blocks auxin dependent lateral root formation, indicating that Tolmetin blocks auxin response.

Auxin responsiveness has also been assessed using the *Arabidopsis* DR5::GUS transgenic line in which several auxin response elements are fused upstream of the GUS reporter gene (Ni et al., 2001). Normally, treatment of DR5::GUS lines with exogenous auxin leads to increased GUS levels, which can be visualized through accumulation of blue color upon adding X-Gluc. Whereas addition of 100 nM NAA or 750 nM IAA to DR5::GUS lines results in increased GUS activity in both the root tip and the mature region of the root, treatment with as little as 10 µM PA greatly reduces the amount of blue staining even in the presence of exogenous auxin. This was also true following treatment with 100 µM Tolmetin, which not only blocked auxin dependent accumulation of GUS in root tips, but prevented staining in the area of lateral root development following exposure to IAA (FIG. 8). Treatment with 100 µM PA completely abolished GUS activity throughout the root, with roots identical to what is seen following treatment with a known anti-auxinic compound, PUB.

TIR1 is Important for Maintaining Hypocotyl and Root Elongation in Etiolated Seedlings Loss of proper auxin signaling as in the dominant shy2-2 mutant (Tian et al., 2003), which fails to have proper turnover of the IAA3 repressor of auxin response, leads to severe hypocotyl shortening for etiolated seedlings (Robles et al., 2012). This argues that proper auxin signaling is required for hypocotyl elongation and is consistent with our results in which treatment with PA leads to moderate inhibition of hypocotyl and root elongation. It was of interest to determine what effect PA might have on hypocotyl and root elongation for loss-of-function mutants representing members of the *Arabidopsis* family of auxin receptors. It was predicted that mutants for receptors with a more prominent role in auxin dependent maintenance of organ elongation would be more severely affected by PA treatment due to the additive effect of the loss-of-function mutation with the effect of this anti-auxinic compound.

For analysis of the role of the various receptors in hypocotyl elongation, Col-0 wt and loss-of-function mutants for all of the auxin receptors (Si-Ammour et al., 2011) except AFB5 were grown for 4 d in the dark in the absence or presence of 30 µM PA on media supplemented with 5 µM $AgNO_3$, which was included to eliminate the negative effect of ethylene on hypocotyl elongation. Inclusion of PA resulted in varied levels of inhibition of hypocotyl elongation for each of the receptor knockout mutants compared to Col-0 wt. The inhibitory effect of PA was enhanced for tir1-1, suggesting that TIR1 makes a significant contribution to maintenance of hypocotyl elongation.

A similar result was found for tir1-1 roots. For this experiment, seedlings were grown in the dark for 4 d in the absence or presence of 30 µM PA after which root length was measured. While PA treatment had a comparable negative effect on root growth of Col-0 wt, afb1-5, afb2-3, afb3-5, and afb4-1, tir1-1 roots were significantly more inhibited by PA. This was confirmed by analysis of growth of Col-0 wt and tir1-1 roots across a range of PA concentrations. In support of the findings for PA on growth of tir1-1 roots, application of an increasing range of Tolmetin revealed that tir1-1 is also hypersensitive to this anti-auxin. These results indicate that TIR1 plays a central role in maintaining auxin dependent root and hypocotyl elongation in *Arabidopsis* likely in combination with one or more of the other auxin receptors that are likely chemical targets of PA and Tolmetin.

Modeling Suggests that PA and Tolmetin Inhibit Auxin-Dependent Protein Complexes Because of the likelihood that PA and Tolmetin are anti-auxins and their structural similarity to NAA and IAA respectively, it was modeled whether PA and Tolmetin could occupy the auxin binding site of TIR1 and inhibit its function. TIR1 can directly bind to auxin and following this, forms a complex with a target of the SCF complex (Dharmasiri et al., 2005) in preparation for its proteolytic degradation. For promotion of auxin signaling, the SCF complex targets for turnover the IAA class of proteins, which function to repress auxin signaling. Because of these connections, it was modeled whether PA or Tolmetin could block auxin-dependent recruitment of IAA7 by TIR1. Proper auxin-dependent assembly of the TIR1-IAA7 complex is in part dependent on proper positioning of F82 of TIR1, which allows IAA7 to associate with TIR1 following auxin binding. Molecular modeling suggests that PA can be accommodated in the auxin binding pocket of TIR1, although the bulky nature of PA would likely result in F82 of TIR1 being improperly aligned and would cause IAA7 to bind in a non-preferred manner. Tolmetin is also predicted to fit into the auxin binding pocket of TIR1 but in an orientation that would not allow for proper positioning of the IAA7 degron for binding to TIR1.

Even though the molecular modeling suggests that both PA and Tolmetin are competitive inhibitors of auxin for binding to TIR1, it has not been possible to demonstrate in vitro that either blocks assembly of the TIR1-IAA7 complex in the presence of auxin. It should be noted that based on our growth analysis with various loss-of-function mutants for auxin receptors, it is likely that one or more of the other receptors are affected to a greater extent than TIR1 by each of these chemicals. This suggests that while TIR1 is convenient for molecular modeling due to the amount of information available regarding it, it might not necessarily be a primary target for PA or Tolmetin in vivo.

Discussion

Ethylene signaling is a key process in regulating plant growth and development including several important agricultural and horticultural phenomena. A better understanding of ethylene signaling is critical for control of these processes. Hormonal crosstalk that occurs between auxin and ethylene is important for progression of these phenomena, yet the biochemical basis for this remains to be elucidated. By screening for chemicals that prevent apical hook formation in an *Arabidopsis* mutant with constitutive ethylene response, ctr1-3, Pamoic acid and Tolmetin were identified and determined to have both anti-ethylene and anti-auxin properties, thus making these useful tools for dissecting the relationship between the two hormones.

While treatment with PA or Tolmetin has pronounced effects on manifestation of ethylene phenomena, they likely do not directly target ethylene signaling but instead inhibit the auxin-response pathway, which serves as a positive regulator of the level of ethylene response (Robles et al., 2012). Several key pieces of evidence support the role of PA and Tolmetin as anti-auxins including their structure, which in the case of PA is similar to two covalently linked molecules of the synthetic auxin NAA. Analysis of the effects of PA or Tolmetin on plant growth shows that treatment with either limits several auxin-related phenomena including root gravitropism. Finally, molecular modeling suggests that PA or Tolmetin inhibit auxin binding to one of its documented receptors, TIR1, thus blocking assembly with its target. From these results, it is highly likely that PA and Tolmetin function as anti-auxins, thus blocking auxin-related phenomena including control of the level of ethylene response.

Prior work has argued that auxin in part conditions ethylene response through control of the level of expression of a subset of genes (Robles et al., 2012). Several reports have provided clues regarding the relationship between auxin and control of ethylene response. Many of these have relied on analysis of auxin response mutants, with these mutants also having altered ethylene response. An excellent example is IAA3 for which both dominant and recessive mutants exist. shy2-2 is a dominant mutant that prevents proper turnover of the transcriptional repressor, IAA3 (Tian et al., 2003). In conjunction with failure to degrade IAA3, shy2-2 mutants have features of ethylene insensitivity including failure to produce an apical hook and maintenance of root growth even in saturating ethylene. In contrast, a loss-of-function mutant for IAA3 (shy2-31) has enhanced ethylene response (Robles et al., 2012), as shown by exaggeration of hypocotyl shortening, likely due to increased auxin signaling. This is also true for the sar1-7 mutant, which represents a loss-of-function mutant affecting a nucleoporin required for proper processing of mRNA's including those encoding various IAA proteins (Parry et al., 2006; Robles et al., 2012). Because IAA repressor proteins are not properly expressed, sar1-7 is auxin hypersensitive in conjunction with having an enhanced ethylene response (Robles et al., 2012). Consequently, auxin is likely a positive regulator of ethylene response and is absolutely required for manifestation of such ethylene-regulated phenomena as apical hook formation.

Other *Arabidopsis* mutants also point to an intrinsic relationship between auxin and ethylene signaling. For example, a tir1 loss-of-function mutant is weakly ethylene insensitive (Alonso et al., 2003). As previously noted, TIR1 encodes one of six F-box proteins that participate in the SCF complex to facilitate turnover of IAA repressor proteins in an auxin dependent manner. This is also true when one considers that blockage of auxin biosynthesis either genetically, as in the case of taa1 or tar2 (Stepanova et al., 2008), or chemically, as in the case of L-kyurenine (He et al., 2011), limits or prevents ethylene response. Interestingly, as with treatment with pamoic acid, these only prevent apical hook formation and/or root growth inhibition, but do not restore hypocotyl elongation. It is likely that loss of auxin biosynthesis or response would lead to failure to promote cell elongation in the hypocotyl, which could not be overcome even though ethylene response was limited or blocked. Such a scenario for auxin being required for hypocotyl elongation is supported by our study of the effects of Pamoic acid and Tolmetin on various auxin receptor loss-of-function mutants. From these results, it is clear that TIR1 plays a prominent role in promoting hypocotyl and root elongation, with a tir1 loss-of-function mutant being more severely inhibited by PA or Tolmetin likely because of the combined effects from reduced auxin signaling due to the loss of a critical receptor and chemical inhibition of one or more of the remaining family members.

Several insights regarding the linkage between auxin and ethylene have been made through the use of Pamoic acid and Tolmetin, suggesting a possible mechanism by which auxin controls the level of ethylene response. These results can be combined with previous observations with sar1, shy2, arf7, and arf19 mutants for which it was argued that a subset of IAA and ARF proteins are required for normal ethylene response. In this model, IAA3, ARF7 and ARF19 have a direct effect on ethylene response (Li et al., 2006), with mutations that enhance auxin response, such as loss of IAA3 in shy2-31, also increasing ethylene response. Conversely, mutations that block auxin response, such as loss of either ARF7 in arf7-1 or ARF19 in arf19-1, result in limitation of ethylene response. Further analysis through study of the effect of IAA on ethylene dependent growth inhibition showed that auxin has an additive effect on ethylene response, with increasing levels of auxin acting synergistically with ethylene (Robles et al., 2012).

Pamoic acid, which likely inhibits auxin binding to the family of F-box auxin receptors, revealed a molecular link between auxin and ethylene signaling at the level of gene expression. There are currently two known mechanisms that regulate the magnitude of ethylene response. The first depends on proper turnover of signaling factors to limit the level of ethylene response, with EIN2 and EIN3 regulated in a manner dependent on proteolytic removal (Binder et al., 2007; Gagne et al., 2004; Guo and Ecker, 2003; Ju et al., 2012; Potuschak et al., 2003; Qiao et al., 2012; Wen et al., 2012). Failure to degrade these leads to inappropriate persistence of the factors and increased expression of EIN3-regulated genes. The second mechanism is more cryptic, with several mutants with enhanced ethylene response having been isolated that do not fit the model relating to turnover of EIN2 and EIN3. These mutants, including eer4, eer5, and fer, have extreme ethylene response in conjunction with failure to upregulate a poorly defined subset of genes whose products likely play a role in regulating the magnitude of ethylene response (Christians et al., 2008; Deslauriers et al., 2010; Robles et al., 2007). Interestingly, a study of FERONIA, which is required for normal brassinosteroid signaling, suggests that brassinosteroids play an opposite role from auxin and oppose ethylene response in conjunction with promoting expression of this subset of genes (Deslauriers and Larsen, 2010). Loss of expression of these genes leads to failure to dampen ethylene response and the severe ethylene phenotype seen for these mutants.

In conjunction with conferring reduced ethylene response, PA increases expression of the aforementioned group of genes that are correlated with enhanced ethylene response. Effectively, auxin seems to regulate the magnitude of ethylene response by dampening the level of expression of this subset of genes. This is supported by several results, suggesting that auxin represents a rheostat for controlling the level of their expression and consequently the magnitude of ethylene response. Whereas the anti-auxin PA increases ethylene responsive expression of members of this subset, treatment of etiolated seedlings with ethylene and auxin almost completely eliminates their expression in conjunction with causing a severe ethylene response at the level of growth. To further support this, sar1-7, which has increased ethylene response likely due to the mutant being auxin hypersensitive, has pronounced reduction in AtEBP expression compared to wt. In conjunction with partial rescue of the sar1-7 phenotype by addition of PA, expression of AtEBP is also restored in the mutant. PA treatment reveals that other ethylene responsive genes are also regulated by auxin, with auxin likely serving as a rheostat for their expression levels. This is particularly true for two pathogen defense genes, chiB and PDF1.2, with auxin being required for their expression and excess auxin resulting in hyperexpression of these genes. In the end, our results suggest a model in which auxin controls ethylene response through fine-tuning of ethylene dependent gene expression and indicates that regulation of auxin response may be an effective way to regulate the manifestation and progression of ethylene dependent phenomena.

REFERENCES

Abeles F B, Morgan P W, Saltveit M E Jr. 1992. Ethylene in Plant Biology. Ed 2. Academic Press, New York Alonso, J M, Stepanova, A N, Solano, R, Wisman, E, Ferrari, S, Ausubel, F M, Ecker, J R. 2003. Five components of the ethylene-response pathway identified in a screen for weak ethylene-insensitive mutants in *Arabidopsis*. *PNAS USA* 100, 2992-2997.

Binder, B M, Walker, J M, Gagne, J M, Emborg, T J, Hemmann, G, Bleecker, A B, Vierstra, R D. 2007. The *Arabidopsis* EIN3 binding F-Box proteins EBF1 and EBF2 have distinct but overlapping roles in ethylene-signaling. *Plant Cell* 19, 509-523.

Bleecker A B, Kende H. 2000. Ethylene: a gaseous signal molecule in plants. *Annu Rev Cell Dev Biol* 16, 1-18.

Chao, Q, Rothenberg, M, Solano, R, Roman, G, Terzaghi, W, Ecker, J R. 1997. Activation of the ethylene gas response pathway in *Arabidopsis* by the nuclear protein ETHYLENE INSENSITIVE3 and related proteins. *Cell* 89, 1133-1144.

Christians, M J, Larsen, P B. 2007. Mutational loss of the prohibitin AtPHB3 results in an extreme constitutive ethylene response phenotype coupled with partial loss of ethylene-inducible gene expression in *Arabidopsis* seedlings. *Journal of Experimental Botany* 58, 2237-2248.

Christians, M J, Robles, L M, Zeller, S M, Larsen, P B. 2008. The eery mutation, which affects a novel proteasome-related subunit, indicates a prominent role for the COPS signalosome in resetting the ethylene-signaling pathway in *Arabidopsis*. *Plant Journal* 55, 467-477.

Deslauriers, S D, Larsen, P B. 2010. FERONIA is a key modulator of brassinosteroid and ethylene responsiveness in *Arabidopsis* hypocotyls. *Molecular Plant* 3, 626-640.

Dharmasiri, N, Dharmasiri, S, Estelle, M. 2005. The F-box protein TIR1 is an auxin receptor. *Nature* 435, 441-445.

Emsley P, Cowtan K. 2004. Coot: model-building tools for molecular graphics. Acta Crystallogr D Biol Crystallogr 60, 2126-2132.

Gagne J M, Smalle J, Gingerich D J, Walker J M, Yoo S-D, Yanagisawa S, Vierstra R D. 2004. *Arabidopsis* EIN3-binding F-box 1 and 2 form ubiquitin-protein ligases that repress ethylene action and promote growth by directing EIN3 degradation. *PNAS USA* 101, 6803-6808.

Guo, H, Ecker, J R. 2003. Plant responses to ethylene gas are mediated by $SCF^{EBF1/EBF2}$ dependent proteolysis of EIN3 transcription factor. *Cell* 115, 667-677.

Haynes D A, Jones W, Motherwell W D S. 2005. A systematic study of lutidine salts formed with the pharmaceutically acceptable salt-forming agent, pamoic acid. *Cryst Eng Comm* 7, 538-543.

He W, Brumos J, Li H, Ji Y, Ke M, Gong X, Zeng Q, Li W, Zhang X, An F, Wen X, Li P, Chu J, Sun X, Yan C, Yan N, Xie D Y, Raikhel N, Yang Z, Stepanova A N, Alonso J M, Guo H. 2011. A small-molecule screen identifies L-kynurenine as a competitive inhibitor of TAA1/TAR activity in ethylene-directed auxin biosynthesis and root growth in *Arabidopsis*. *Plant Cell* 23, 3944-3960.

Hua, J, Meyerowitz, E M. 1998. Ethylene responses are negatively regulated by a receptor gene family in *Arabidopsis thaliana*. *Cell* 94, 261-271.

Ju C, Yoon G M, Shemansky J M, Lin D Y, Ying Z I, Chang J, Garrett W M, Kessenbrock M, Groth G, Tucker M L, Cooper B, Kieber J J, Chang C. 2012. CTR1 phosphorylates the central regulator EIN2 to control ethylene hormone signaling from the ER membrane to the nucleus in *Arabidopsis*. *PNAS USA* 109, 19486-19491.

Kieber, J J, Rothenberg, M, Roman, G, Feldmann, K A, Ecker, J R. 1993. CTR1, a negative regulator of the ethylene response pathway in *Arabidopsis*, encodes a member of the Raf family of protein kinases. *Cell* 72, 427-441.

Li J, Dai X, Zhao Y. 2006. A role for AUXIN RESPONSE FACTOR 19 in auxin and ethylene signaling in *Arabidopsis*. *Plant Physiology* 140, 899-908.

McDaniel B K, Binder B M. 2012. ethylene receptor 1 (etr1) is sufficient and has the predominant role in mediating inhibition of ethylene responses by silver in *Arabidopsis thaliana*. *J Biol Chem* 287, 26094-26103.

Ni D A, Wang L J, Ding C H, Xu Z H. 2001. Auxin distribution and transport during embryogenesis and seed germination of *Arabidopsis*. *Cell Res* 11, 273-278.

Parry G, Ward S, Cernac A, Dharmasiri S, Estelle, M. 2006. The *Arabidopsis* SUPPRESSOR OF AUXIN RESISTANCE proteins are nucleoporins with an important role in hormone signaling and development. *Plant Cell* 18, 1590-15603.

Potuschak T, Lechner E, Parmentier Y, Yanagisawa S, Grava S, Koncz C, Genschik P. 2003. EIN3-dependent regulation of plant ethylene hormone signaling by two *Arabidopsis* F box proteins EBF1 and EBF2. *Cell* 115, 679-689.

Qiao H, Shen Z, Huang S S, Schmitz R J, Urich M A, Briggs S P, Ecker J R. 2012. Processing and subcellular trafficking of ER-tethered EIN2 control response to ethylene gas. *Science* 338, 390-393.

Robles, L M, Wampole, J S, Christians, M J, Larsen, P B. 2007. *Arabidopsis* enhanced ethylene response 4 encodes an EIN3-interacting TFIID transcription factor required for proper ethylene response, including ERF1 induction. *Journal of Experimental Botany* 58, 2627-2639.

Robles, L M, Deslauriers S D, Alvarez A A, Larsen P B. 2012. A loss-of-function mutation in the nucleoporin AtNUP160 indicates that normal auxin signalling is required for a proper ethylene response in *Arabidopsis*. *J Exp Bot* 63, 2231-2241.

Rodriguez F I, Esch J J, Hall A E, Binder B M, Schaller G E, Bleecker A B. 1999. A copper cofactor for the ethylene receptor ETR1 from *Arabidopsis*. *Science* 283, 5105-5109.

Si-Ammour A, Windels D, Arn-Bouldoires E, Kutter C, Ailhas J, Meins F Jr, Vazquez F. 2011. miR393 and secondary siRNAs regulate expression of the TIR1/AFB2 auxin receptor Glade and auxin-related development of *Arabidopsis* leaves. *Plant Physiology* 157, 683-691.

Sisler E C. 2006. The discovery and development of compounds counteracting ethylene at the receptor level. *Biotechnol Adv* 24, 357-367.

Solano, R, Stepanova, A, Chao, Q, Ecker, J R. 1998. Nuclear events in ethylene-signaling: a transcriptional cascade mediated by ETHYLENE-INSENSITIVE3 and ETHYLENE RESPONSE-FACTOR1. *Genes and Development* 12, 3703-3714.

Stepanova, A N, Robertson-Hoyt, J, Yun, J, Benavente, L M, Xie, D Y, Dolezal, K, Schlereth, A, Jurgens, G, Alonso, J M. 2008. TAA1-mediated auxin biosynthesis is essential for hormone crosstalk and plant development. *Cell* 133, 177-191.

Stepanova, A N, Alonso, J M. 2009. Ethylene signaling and response: where different regulatory modules meet. *Current Opinion in Plant Biology* 12, 548-555.

Tan X, Calderon-Villalobos L I, Sharon M, Zheng C, Robinson C V, Estelle M, Zheng N. 2007. Mechanism of auxin perception by the TIR1 ubiquitin ligase. *Nature* 446, 640-645.

Tian, Q, Nagpal, P, Reed, J W. 2003. Regulation of *Arabidopsis* SHY2/IAA3 protein turnover. *Plant Journal* 36, 643-651.

Trott O, Olson A J. 2010. AutoDock Vina: improving the speed and accuracy of docking with a new scoring function, efficient optimization and multithreading. *J Comp Chem* 31, 455-461.

Wen X, Zhang C, Ji Y, Zhao Q, He W, An F, Jiang L, Guo H. 2012. Activation of ethylene signaling is mediated by nuclear translocation of the cleaved EIN2 carboxyl terminus. *Cell Res* 22, 1613-1616.

The examples and embodiments described herein are for illustrative purposes only and that various modifications or changes in light thereof are to be included within the spirit and purview of this application and scope of the appended claims. All publications, internet sources, database entries, patents, and patent applications cited herein are hereby incorporated by reference in their entireties for all purposes.

What is claimed is:

1. A method of inhibiting at least one auxin response in a plant comprising:
   contacting the plant with an effective amount of a compound of Formula I:

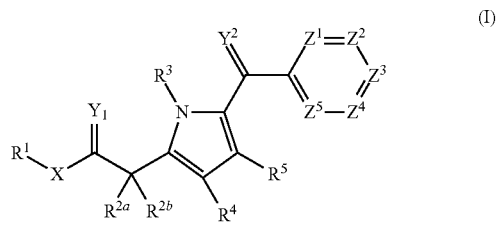

or a salt thereof, wherein:
$R^1$ is hydrogen;
$R^3$ is hydrogen or $C_{1-6}$ alkyl;
X is O;
each Y is O;
each Z (i.e., each of $Z^{1-5}$) is $C(R^6)$;
each $R^2$, $R^4$, and $R^5$ is hydrogen; and
each $R^6$ is independently selected front the group containing hydrogen, $C_{1-4}$ alkyl, and halo,
thereby inhibiting at least one auxin response in the plant.

2. The method of claim 1, wherein the compound is tolmetin or a salt thereof.

3. The method of claim 1, wherein the compound is applied in solution at a concentration of 1-100 micromolar.

4. The method of claim 1, wherein the at least one auxin response is selected from the group consisting of: hypocotyl elongation, fruit ripening, root growth, gravitropic response, phototropic response, citrus regreening, fertility, floral development, and leaf and stem growth.

5. The method of claim 1, wherein the compound is applied to a plant part.

6. The method of claim 1, further comprising detecting the at least one auxin response in the plant.

7. The method of claim 5, wherein the plant part is a plant cutting and after the contacting the plant cutting is submitted to storage or transport.

8. The method of claim 1, wherein $R^3$ is hydrogen.

9. The method of claim 1, wherein $R^3$ is $C_{1-4}$ alkyl.

10. The method of claim 1, wherein $R^6$ is chloride.

11. The method of claim 1, wherein $R^6$ is $C_{1-2}$ alkyl.

12. The method of claim 9, wherein $R^3$ is methyl.

13. The method of claim 11, wherein the —$CZ^5$ ring is a p-methylphenyl group.

* * * * *